(12) United States Patent
Kafri et al.

(10) Patent No.: US 7,220,578 B2
(45) Date of Patent: May 22, 2007

(54) SINGLE LTR LENTIVIRUS VECTOR

(76) Inventors: Tal Kafri, 208 Blueridge Rd., Carrboro, NC (US) 27510; Hong Ma, 127 Gratiot Dr., Morrisville, NC (US) 27560

( * ) Notice: Subject to any disclaimer, the term of this patent is extended or adjusted under 35 U.S.C. 154(b) by 0 days.

(21) Appl. No.: 10/721,563

(22) Filed: Nov. 25, 2003

(65) Prior Publication Data

US 2004/0170962 A1 Sep. 2, 2004

Related U.S. Application Data

(60) Provisional application No. 60/429,635, filed on Nov. 27, 2002.

(51) Int. Cl.
- C12N 15/00 (2006.01)
- C12N 15/48 (2006.01)
- C12N 15/867 (2006.01)
- C12N 15/64 (2006.01)
- C07H 21/04 (2006.01)

(52) U.S. Cl. ................. 435/320.1; 536/23.1; 536/24.1; 435/455; 435/456; 435/91.41

(58) Field of Classification Search ................. 435/5, 435/69.3, 235.1, 456, 325, 320.1; 536/23.72
See application file for complete search history.

(56) References Cited

OTHER PUBLICATIONS

Naldini, L. et al., "Efficient transfer, integration, and sustained long-term expression of the transgene in adult rat brains injected with a lentiviral vector", 1996, PNAS, vol. 93: pp. 11382-11388.*
Naldini, L. et al., "In Vivo Gene Delivery and Stable Transduction of Nondividing Cells by a Lentiviral Vector", 1996, Science, vol. 272: pp. 263-267.*
Rausch, J.W. et al., "Binding, bending, and bonding: polypurine tract-primed initiation of plus-strand DNA synthesis in human immunodeficiency virus", 2004, Int. J. of Biochem. and Cell Biol., vol. 36: pp. 1752-1766.*
Hannon, G. et al., "MaRX: An Approach to Genetics in Mammalian Cells", 1999, Science, vol. 283: pp. 1129-1130.*
Ma, H. et al., "A Single-LTR HIV-1 Vector Optimized for Functional Genomics Applications", 2004, Mol. Therapy, vol. 10: pp. 139-149.*
Brown, P.O. (1997). Integration, In *Retroviruses* (Coffin, J.M., Hughes, S.H., Varmus, H.E., Eds.), pp. 161-203. Cold Spring Harbor Laboratory Press, Plainview, New York.
Kafri, T. (2001). Lentivirus vectors: difficulties and hopes before clinical trials. *Curr. Opin. Mol. Ther.* 3: 316-326.
Kafri, T., van Praag, H., Ouyang, L., Gage, F.H. and Verma, I.M. (1999). A packaging cell line for lentivirus vectors. *J. Virol.* 73:576-584.
Kafri, T. (2004). Gene Delivery by Lentivirus Vectors: An Overview, In *Gene Delivery to Mammalian Cells, vol. 2, Viral Gene Transfer Techniques* (Heiser, W.C., Eds.), pp. 367-390. Humana Press Inc., Totowa, New Jersey.
Kilzer, J.M., Stracker, T., Beitzel, B., Meek, K., Weitzman, M. and Bushman, F.D. (2003). Roles of host cell factors in circularization of retroviral DNA. *Virology* 314: 460-467.

Koh, E.Y., Chen, T. and Daley, G.Q. (2002). Novel retroviral vectors to facilitate expression screens in mammalian cells. *Nucleic Acids Res.* 30: e142. (7 pp.).
Li, L., Olvera, J.M., Yoder, K.E., Mitchell, R.S., Butler, S.L., Lieber, M., et al. (2001). Role of the non-homologous DNA end joining pathway in the early steps of retroviral infection. *Embo J.* 20: 3272-3281.
Miyoshi, H., Blomer, U., Takahashi, M., Gage, F.H. and Verma, I.M. (1998). Development of a self-inactivating lentivirus vector. *J. Virol.* 72: 8150-8157.
Nakajima, N., Lu, R. and Engelman, A. (2001). Human immunodeficiency virus type 1 replication in the absence of integrase-mediated DNA recombination: Definition of permissive and nonpermissive T-cell lines. *J. Virol.* 75: 7944-7955.
Oh, J., Julias, J.G., Ferris, A.L. and Hughes, S.H. (2002). Construction and characterization of a replication-competent retroviral shuttle vector plasmid. *J. Virol.* 76: 1762-1768.
Van Lint, C., Amella, C.A., Emiliani, S., John, M., Jie, T. and Verdin, E. (1997). Transcription factor binding sites downstream of the human immunodeficiency virus type 1 transcription start site are important for virus infectivity. *J. Virol.* 71: 6113-6127.
Verdin, E. and Van Lint, C. (1995). Internal transcriptional regulatory elements in HIV-1 and other retroviruses. *Cell Mol. Biol.* (Noisy-le-grand) 41: 365-369.
Walhout et al. "GATEWAY Recombinatorial Cloning: Application to the Cloning of Large Numbers of Open Reading Frames of ORFeomes" *Methods in Enzymology* 328:575-592 (2000).
Wu, Y. and Marsh, J.W. (2001). Selective transcription and modulation of resting T cell activity by preintegrated HIV DNA. *Science* 293: 1503-1506.
Xu, K., Ma, H., McCown, T.J., Verma, I.M. and Kafri, T. (2001). Generation of a stable cell line producing high-titer self-inactivating lentiviral vectors. *Mol. Ther.* 3: 97-104.
Zufferey, R., Dull, T., Mandel, R.J., Bukovsky, A., Quiroz, D., Naldini, L., et al. (1998). Self-inactivating lentivirus vector for safe and efficient in vivo gene delivery. *J. Virol.* 72: 9873-9880.

* cited by examiner

*Primary Examiner*—Scott D. Priebe
*Assistant Examiner*—Michael Burkhart
(74) *Attorney, Agent, or Firm*—Myers, Bigel, Sibley & Sajovec, P.A.

(57) ABSTRACT

The present invention provides an isolated nucleic acid comprising a single retroviral LTR, a polypurine tract, a packaging signal, a primer binding site and a rev responsive element. Further provided is an isolated nucleic acid comprising a heterologous nucleotide sequence, a single retroviral long terminal repeat (LTR), a packaging signal, a rev responsive element, a polypurine tract, a eukaryotic promoter, a primer binding site, a bacterial origin of replication and a bacterial selection marker. In addition, the present invention provides an isolated nucleic acid comprising a 5' retroviral LTR and a 3' retroviral LTR, a heterologous nucleotide sequence, a packaging signal, a rev responsive element, a polypurine tract, a eukaryotic promoter, a primer binding site, a bacterial origin of replication and a bacterial selection marker cassette, wherein the bacterial origin of replication and bacterial selection marker are located between the two LTRs.

12 Claims, 12 Drawing Sheets

SINGLE LTR LENTIVIRUS VECTOR

CROSS-REFERENCE TO RELATED APPLICATION

The present application claims the benefit of U.S. Provisional Application No. 60/429,635 filed Nov. 27, 2002, the disclosure of which is incorporated by reference herein in its entirety.

FIELD OF THE INVENTION

The present invention relates generally to novel recombinant retrovirus constructs. More specifically, the present invention relates to retroviral vector constructs comprising a single retroviral long terminal repeat (LTR) and compositions and methods related to these constructs.

BACKGROUND OF THE INVENTION

Retrovirus vectors are common tools used in gene therapy model systems. However, there are many safety concerns associated with the use of such vectors. A consideration in the construction of retroviral packaging cell lines is the production of high titer vector supernatants free of recombinant replication competent retroviruses (RCRs). In particular, one method to reduce the likelihood of generating RCRs in packaging cells is to divide the packaging functions into two genomes, for example, one which expresses the gag and pol gene products and the other which expresses the env gene product (Bosselman et al., Mol. Cell. Biol. (1987) 7(5):1797–1806; Markowitz et al., J. Virol. (1988) 62(4): 1120–1124; Danos & Mulligan, Proc. Natl. Acad. Sci. (1988) 85:6460–6464). This approach minimizes the ability for co-packaging and subsequent transfer of the two genomes, and allows for a significantly decrease in the frequency of recombination to produce RCRs, due to the presence of three retroviral genomes in the packaging cell. High titer retroviral vector stocks have also been generated by a minimal packaging system containing only the gag-pol gene. High titer retroviral HIV-1 vector stocks have also been generated by a minimal packaging system containing only the gag-pol gene and the rev gene. In the event recombinants arise, mutations (Danos & Mulligan, supra) or deletions (Bosselman et al., supra; Markowitz et al., supra) can be configured within the undesired gene products to render any possible recombinants non-functional. In addition, deletion in the 3' LTR in the vector construct further reduces the ability to form functional recombinant particles.

Several research groups have focused on the lentivirus vector system. Lentiviruses are complex retroviruses that contain, in addition to the common retroviral genes gag, pol and env, other genes with regulatory or structural function. A representative example of a lentivirus is human immunodeficiency virus-1 (HIV-1), an etiologic agent of acquired immune deficiency syndrome (AIDS).

In addition to full-length linear HIV-1 DNA, which serves as the precursor to the integrated provirus, nuclei of virus-transduced cells contain quantities of circular viral DNA forms that do not contribute to provirus integration. These forms have been considered as "dead-end by-products of aborted infections," with minimum contribution to the virus life cycle.

It is believed that a retroviral vector construct used in the production of recombinant retroviral particles should have two LTRs, each containing a complete R region, because both are believed to be required for efficient vector production and viral replication. The present invention provides a retroviral vector construct containing only one retroviral LTR that is used to produce high titers of recombinant retroviral particles, thereby reducing the likelihood of recombination and rearrangement during particle formation that can lead to the generation of RCR.

SUMMARY OF THE INVENTION

The present invention provides an isolated nucleic acid comprising a single retroviral LTR, a polypurine tract, a packaging signal, a primer binding site and a rev responsive element.

Further provided is an isolated nucleic acid comprising a heterologous nucleotide sequence, a single retroviral long terminal repeat (LTR), a packaging signal, a rev responsive element, a polypurine tract, a eukaryotic promoter, a primer binding site, a bacterial origin of replication and a bacterial selection marker.

In addition, the present invention provides an isolated nucleic acid comprising a 5' retroviral LTR and a 3' retroviral LTR, a heterologous nucleotide sequence, a packaging signal, a rev responsive element, a polypurine tract, a eukaryotic promoter, a primer binding site, a bacterial origin of replication and a bacterial selection marker cassette, wherein the bacterial origin of replication and bacterial selection marker are located between the two LTRs.

Further provided herein is a method of producing a single-LTR circular HIV-1 form plasmid, comprising: introducing a shuttle vector comprising a nucleic acid of the present invention into a eukaryotic cell; extracting non-integrated DNA from the eukaryotic cell; transforming a bacterial cell with the extracted non-integrated DNA; selecting a bacterial cell showing resistance to a selection marker; and isolating a single-LTR circular HIV-form plasmid from the bacterial cell.

Additionally, the present invention provides a method of making a retroviral vector particle, comprising: introducing an expression cassette comprising a nucleic acid of the present invention comprising only one retroviral LTR into a retroviral packaging cell in medium, said packaging cell comprising helper retroviral constructs encoding rev, gag/pol and env proteins but lacking packaging sequences; and collecting retroviral vector particles from the medium.

The present invention also provides a method of producing a retroviral expression vector, comprising cloning the nucleic acid of claim 1 into a non-retroviral plasmid based expression vector.

Also provided herein is a method of isolating a cDNA sequence that encodes a gene product that results in a particular phenotype upon contact with a test substance, comprising:
 a. producing a cDNA library in a population of nucleic acids as set forth in the present invention;
 b. introducing the nucleic acids of step (a) into eukaryotic cells;
 c. contacting the cells of step (b) with the test substance;
 d. introducing a nucleic acid encoding Cre protein into surviving cells of step (c) under conditions whereby the Cre protein nucleic acid is expressed;
 e. extracting circular DNA from the cells of step (d);
 f. transforming a bacterial cell with the circular DNA of step (e); and
 g. isolating from the bacterial cell the cDNA sequence that encodes a gene product that results in a particular phenotype upon contact with a test substance.

DETAILED DESCRIPTION OF THE INVENTION

Figure 1:
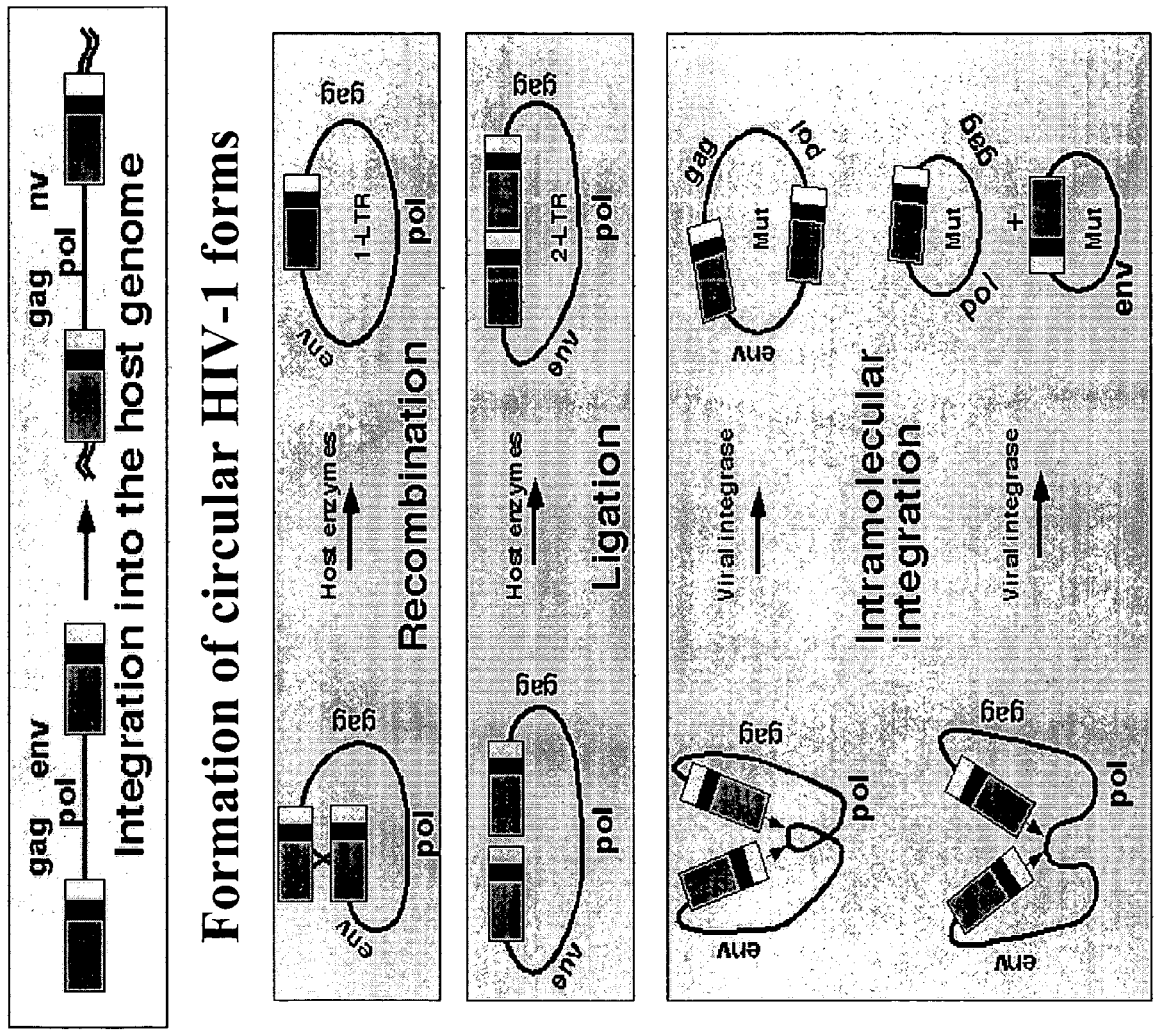
FIG. 1 depicts the formation of circular HIV-1 forms for both one and two LTRs.
Figure 2:
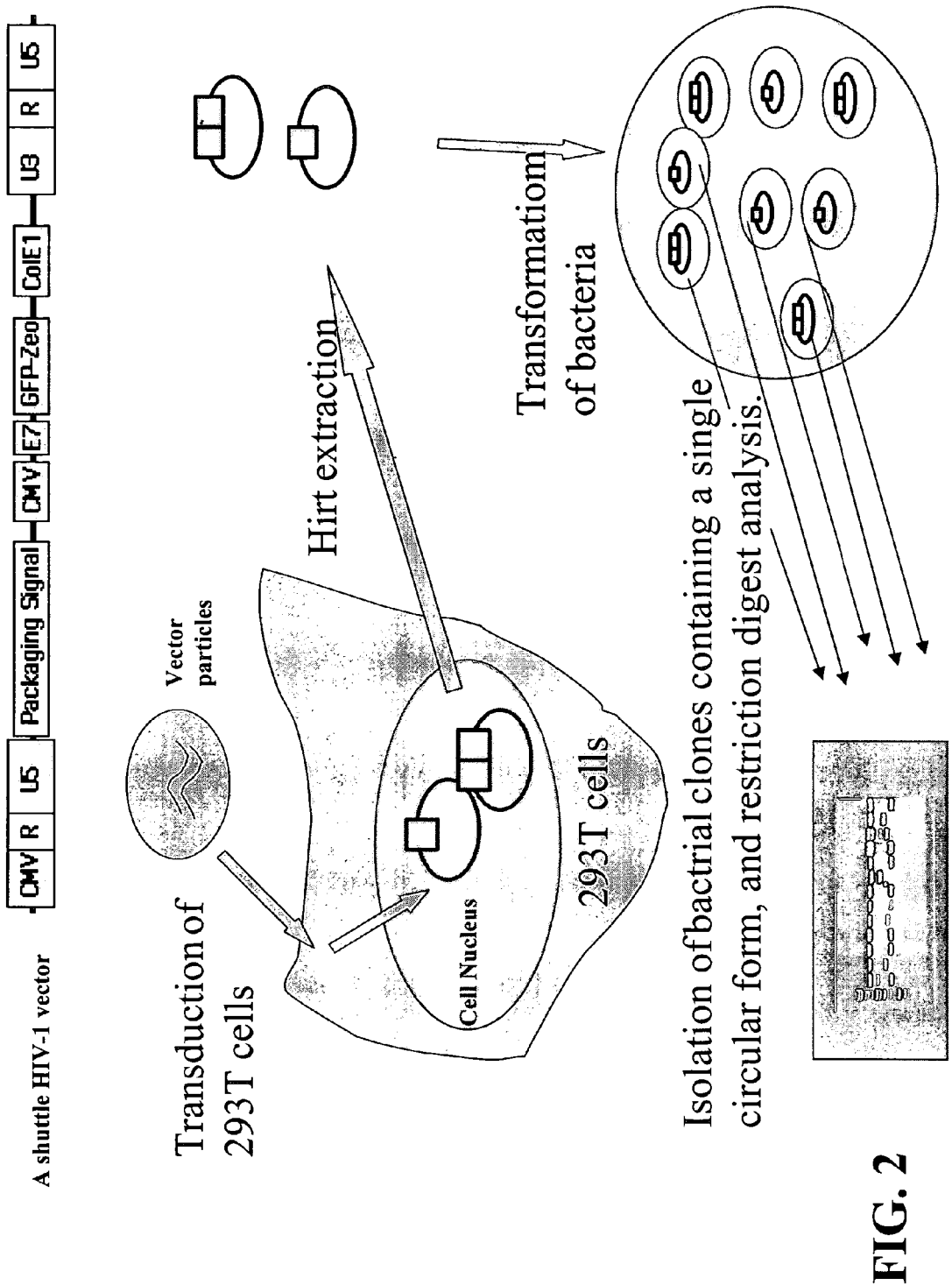
FIG. 2 illustrates the analysis performed of episomal HIV-1 vectors wherein the shuttle HIV-1 vector undergoes the steps of transduction, extraction, transformation and then isolation.

The present invention is described herein with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

All publications, patent applications, patents, and other references mentioned herein are incorporated by reference in their entirety for the teachings described in the sentence and/or paragraphed wherein each is mentioned.

Nucleotides and amino acids are represented herein in the manner recommended by the IUPAC-IUB Biochemical Nomenclature Commission, or (for amino acids) by either the one-letter code, or the three letter code, both in accordance with 37 CFR §1.822 and established usage. See, e.g., *PatentIn User Manual*, 99–102 (November 1990) (U.S. Patent and Trademark Office).

Standard techniques for the construction of the vectors of the present invention are well-known to those of ordinary skill in the art and can be found in such references as Sambrook et al. (1989) *Molecular Cloning: A Laboratory Manual* 2$^{nd}$ Ed. Cold Spring Harbor, N.Y and F. M. Ausubel et el. (1994) *Current Protocols in Molecular Biology* Green Publishing Associates, Inc. and John Wiley & Sons, Inc., New York, N.Y. A variety of strategies are available for ligating fragments of DNA, the choice of which depends on the nature of the termini of the DNA fragments and which choices can be readily made by the skilled artisan.

The term "nucleic acid," "nucleotide sequence," "nucleic acid sequence," "coding sequence," or "gene sequence," as used herein, is intended to refer to a nucleic acid molecule (e.g., DNA or RNA). Such sequences may be derived from a variety of sources including DNA, cDNA, synthetic DNA, mRNA, or combinations thereof. Such sequences may comprise genomic DNA which may or may not include naturally occurring introns. Genomic DNA or cDNA may be obtained in any number of ways. Genomic DNA can be extracted and purified from suitable cells by means well known in the art. Alternatively, mRNA can be isolated from a cell and used to prepare cDNA by reverse transcription, or other means well known in the art.

As used herein, an "isolated" nucleic acid or polypeptide means a nucleic acid or polypeptide separated or substantially free from at least some of the other components of the naturally occurring organism or virus, for example, the cell or viral structural components or other polypeptides or nucleic acids commonly found associated with the nucleic acid or polypeptide.

As used herein, "transduction" or "infection" of a cell by a retrovirus means that the retrovirus enters the cell to establish an active (i.e., lytic) infection. As used herein, "transduction" of a cell by a retrovirus means that the retrovirus enters the cell to establish a latent infection. See, e.g., BERNARD N. FIELDS et al., VIROLOGY, Volume 2, Chapter 69 (3d ed., Lippincott-Raven Publishers).

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotides).

A "fusion nucleic acid" comprises two or more nucleic acid sequences covalently linked together by methods standard in the art. The nucleic acid may be DNA, RNA, or a hybrid thereof. Likewise, a "fusion polypeptide" comprises two or more polypeptides covalently linked together, e.g., by peptide bonding.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects, improvement in transplant survivability, or slows, controls or decreases the likelihood of onset of a condition or disease state.

An "immunogenic polypeptide" is a polypeptide that induces an active immune response in a subject, e.g., for vaccination against a pathogenic organism or cancer.

By the terms "treating" and "treatment" with respect to a particular condition or disease state, it is intended that the severity of the condition or disease state is reduced and/or some beneficial effect is provided to the subject. Alternatively, the terms "treat" or "treatment" may indicate that administration of the retroviral particles of this invention slows, controls, or decreases the likelihood or probability, or delays the onset of the condition or disease state in the subject.

A "therapeutically effective" amount as used herein is an amount that provides sufficient expression of the heterologous nucleotide sequence delivered by the vector to provide some improvement or benefit to the subject. Alternatively stated, a "therapeutically effective" amount is an amount that will provide some alleviation, mitigation, or decrease in at least one clinical symptom in the subject or that will delay, control or decrease the likelihood of onset of a condition or disease state in the subject. Those skilled in the art will appreciate that the therapeutic effects need not be complete or curative, as long as some benefit is provided to the subject.

The present invention is based on the surprising and unexpected discovery that a retroviral construct comprising a single retroviral LTR (i.e., containing no more than one LTR on the construct) can be employed in a variety of methods previously thought to require a retroviral construct comprising two retroviral LTRs.

Thus in one embodiment, the present invention provides an isolated nucleic acid comprising a single retroviral LTR, a polypurine tract, a packaging signal, a primer binding site and a rev responsive element. This nucleic acid is referred to as a minimal KM fragment, that contains all of the cis elements required for retroviral production. The extended KM fragment can further optionally comprise a central polypurine tract and/or a post-transcriptional regulatory element.

In a different embodiment, the present invention provides an isolated nucleic acid comprising a heterologous nucleotide sequence, a single retroviral LTR, a packaging signal, a rev responsive element, a polypurine tract, a eukaryotic promoter, a primer binding site, a bacterial origin of replication and a bacterial selection marker. This nucleic acid can be used as a single-LTR shuttle vector in the methods of the present invention, as described in more detail below.

In a further embodiment, the present invention provides an isolated nucleic acid comprising a 5' retroviral LTR and a 3' retroviral LTR, a heterologous nucleotide sequence, a packaging signal, a rev responsive element, a polypurine tract, a eukaryotic promoter, a primer binding site, a bacterial origin of replication and a bacterial selection marker cassette, wherein the bacterial origin of replication and bacterial selection marker are located between the two LTRs. This nucleic acid can be used as a 2LTR shuttle vector in the methods of the present invention, as described in more detail below.

The nucleic acids described above can further comprise a central polypurine tract and/or a post-transcriptional regulatory element. These retroviral elements and the other elements described in the nucleic acids of this invention can be from any member of the Retroviridae family, which includes, for example, lentiviruses. A representative example of a lentivirus of this invention is HIV-1. Additional representative examples of a retrovirus of this infection can include, but is not limited to, FIV, EIAV, SIV, HIV-2, BIV, VISNA, or simple (Maloney based) retroviruses.

Lentiviral vectors have many advantages as gene-transfer vehicles including transduction of nondividing cells, sustained transgene expression from the integrated provirus, and simplicity in modifying tropism by pseudotyping the lentivirus. HIV-based lentiviral vectors (Naldini et al. (1996) *Science* 272:263–267) pseudotyped with vesicular stomatitis virus envelope glycoprotein (VSV-G) offer the ability to transduce a broad range of different cell types.

In the nucleic acids of this invention comprising a eukaryotic promoter, the promoter can be any promoter, either constitutive or inducible, including synthetic promoters, that can function as a promoter in a eukaryotic cell. For example, the eukaryotic promoter can be, but is not limited to, a CMV promoter, a PGK promoter, an E1F promoter, a SV40 promoter, a RSV promoter, a moMLV promoter, ecdysone inducible promoters, E1a inducible promoters, tetracycline inducible promoters, dimerizing systems, estrogen receptor based promoters, etc., as are well known in the art.

In addition, the nucleic acids of this invention can comprise a selectable marker, which can comprise a promoter and a coding sequence for a selectable trait. Nucleotide sequences encoding selectable markers are well known in the art, and include those that encode gene products conferring resistance to antibiotics or anti-metabolites, or that supply an auxotrophic requirement. Examples of such sequences include, but are not limited to, those that encode thymidine kinase activity, or resistance to methotrexate, ampicillin, kanamycin, chloramphenicol, or zeocin, among many others. Furthermore, the promoter included in the bacterial selection marker can be, but is not limited to, E7.

In a particular embodiment, the nucleic acids of this invention can comprise a retroviral LTR in which a major portion of the U3 region is deleted, to produce a self-inactivating (SIN) vector. A "major portion of the U3 region" is a portion that includes enhancer and promoter sequences but does not include the minimal sequences required for integration located at the 5' end of the U3 region of the LTR. Thus, for example, the ATTS site may be removed. For nucleic acids with two LTRs (i.e., a 5' LTR and a 3' LTR), the deletion is in the U3 region of the 3' LTR.

In addition to deleting a major portion of the U3 region of the LTR to produce a SIN vector, the major portion of the U3 region can be replaced with an inducible promoter (e.g., tetracycline inducible promoter).

In one embodiment, the nucleic acids of the present invention can comprise an LTR comprising a U3 region containing a loxP site or a restriction site. For nucleic acids with two LTRs (i.e., a 5' LTR and a 3' LTR), the loxP site or restriction site is present in the U3 region of the 3' LTR.

The present invention further comprises expression cassettes and vector constructs comprising the nucleic acids of this invention, as well as cells and animals into which the expression cassettes and/or constructs are introduced.

The nucleic acids, expression cassettes and vector constructs of this invention can comprise one or more heterologous (i.e., exogenous) nucleotide sequences. A nucleotide sequence is said to be heterologous if it is not naturally present in the virus from which the vector construct was produced or if it is not naturally present in a target cell into which the nucleic acid comprising the heterologous nucleotide sequence is introduced. The heterologous nucleotide sequence can encode any polypeptide, peptide, antisense or ribozyme sequence. In one embodiment, a heterologous nucleotide sequence can encode a polypeptide or peptide that can impart an immunogenic effect and/or therapeutic effect in a target cell in a subject. As an example, the heterologous nucleotide sequence of this invention can encode a reporter protein, which can include, but is not limited to, green fluorescent protein (GFP), luciferase, human growth hormone and chloramphenicol acetyltransferase (CAT).

It is further contemplated that the nucleic acids, expression cassettes and vector constructs of this invention can be employed in a variety of methods. For example, the present invention provides a method of producing a single-LTR circular HIV-1 form plasmid, comprising: introducing a shuttle vector comprising a nucleic acid of the present invention into a eukaryotic cell; extracting non-integrated DNA from the eukaryotic cell; transforming a bacterial cell with the non-integrated DNA; selecting a bacterial cell showing expression of nucleic acid encoding a selectable marker located on the shuttle vector; and isolating a single-LTR circular HIV-form plasmid from the bacterial cell.

The shuttle vector of this method can be a nucleic acid of this invention comprising a bacterial origin of replication and any selectable bacterial marker, as would be well known in the art. The eukaryotic cell of this invention can be any eukaryotic cell capable of being transduced or transfected with a shuttle vector, and can be, for example, but is not limited to 293T cells and SODk1 cells. Furthermore, methods of extracting non-integrated DNA from cells, such as HIRT or mini-prep plasmid protocols, are well known in the art.

In a further embodiment, the present invention provides a method of making a retroviral vector particle, comprising introducing a nucleic acid of the present invention comprising only one retroviral LTR into a retroviral packaging cell in medium, said packaging cell comprising nucleotide sequences encoding rev, gag/pol and env proteins but lacking packaging sequences; and collecting retroviral vector particles from the medium.

Methods for producing retroviral packaging cells and for producing retroviral particles in these cells are well known in the art. For example, the packaging cell may constitutively or inducibly express the rev, gag/pol and env proteins from genes integrated into the genome of the packaging cell. Alternatively, the rev, gag/pol and env protein coding sequences can be introduced into the cell and transiently expressed at the same time or around the same time the nucleic acid comprising a single LTR is introduced into the cell. These nucleic acids can be introduced into the packaging cell via any means known for the introduction of nucleic acid into cells (e.g., electroporation, transduction, lipofection, etc.). The resulting retroviral vector particles produced in the packaging cell are released into the medium surrounding the packaging cells in culture and are collected from the medium by well-known methods for collecting virus particles.

In one embodiment of this invention, the packaging cell can comprise a nucleotide sequence encoding an envelope protein from another virus, and thus does not comprise a nucleotide sequence encoding the retroviral env protein. As an example, the packaging cell can comprise a nucleotide sequence encoding VSV-G protein, wherein the nucleotide sequence is integrated into the genome of the packaging cell and expressed constitutively or under the control of an inducible promoter. Alternatively, the nucleotide sequence encoding VSV-G protein can be introduced into the packaging cell to be expressed transiently, at or around the same time that the nucleic acid comprising a single LTR is introduced into the packaging cell. The resulting vector particles will contain the VSV-G protein, rather than the retroviral env protein on the particle surface.

It is also contemplated that retroviral vector particles can be produced from a cell that expresses a nucleotide sequence encoding a virus envelope protein (e.g., VSV-G protein) and a separate cell that expresses nucleotide sequences encoding rev and gag/pol. These respective cells can have these nucleotide sequences integrated into the cell. genome, from which these sequences are expressed constitutively or under the direction of an inducible promoter, or these cells can express these nucleotide sequences transiently from constructs introduced into these cells. A nucleic acid vector (e.g., a nucleic acid-of this invention comprising a single LTR) is introduced into the cells producing the rev and gag/pol proteins. The supernatants of these respective cell cultures are combined and subjected to ultracentrifugation at e.g., 50,000 g for about two hours. The ultracentrifugation forces bring the envelope protein and encapsidated vector together, resulting in formation of a stable structure comprising the encapsidated vector and envelope proteins, which does not require additional materials to keep these components together. These particles can be efficiently transformed in vivo. In the example wherein the virus envelope protein is VSV-G, the resulting vector particles will contain the VSV-G protein on the particle surface. This method further reduces the chances of generating RCR during production of retroviral vector particles.

The discovery of the KM fragment further provides for the production of retroviral vectors from non-retroviral plasmid-based vectors in a single cloning step. Thus, further provided in the present invention is a method of producing a retroviral expression vector, comprising cloning the nucleic acid of the KM fragment into a non-retroviral plasmid based expression vector. The KM fragment can be cloned into the non-retroviral vector by replacing a polyA site in the non-retroviral vector sequence that is in the transcription orientation. The present invention further provides a retroviral expression vector produced by this method.

The non-retroviral plasmid-based expression vector can be any expression vector into which the KM fragment can be cloned according to standard methods of cloning. Examples of non-retroviral vectors that can be employed in this method include, but are not limited to, viral based vectors (e.g., AAV-based vectors, adenovirus-based vectors, herpesvirus based vectors, alphavirus-based vectors, etc.)

In a further embodiment, the nucleic acids of this invention can be employed in methods for screening test substances and/or for selecting genes that manifest a specific and/or particular phenotype upon exposure to and/or contact with various substances. A test substance as used herein can be any chemical, drug, reagent, virus, pathogenic agent, compound, etc., that can be contacted with cells. "Exposure to" or "contact with" a substance can include, but is not limited to, physical contact, irradiation, exposure to light, infection, temperature alteration, pH alteration, $CO_2$ alteration, etc.

For example, the present invention provides a method of isolating a cDNA sequence that encodes a gene product that results in a particular phenotype upon contact with a test substance, comprising: -producing a cDNA library in a population of nucleic acids as set forth in the present invention, wherein the nucleic acid comprises a retroviral LTR comprising a loxP site or a restriction site in the U3 region; introducing said nucleic acids into eukaryotic cells; contacting the cells with a test substance under conditions whereby a particular phenotype is produced; introducing a nucleic acid encoding Cre protein into cells having the particular phenotype, under conditions whereby the Cre protein nucleic acid is expressed; extracting circular DNA from the eukaryotic cells; transforming a bacterial cell with the circular DNA; and isolating from the bacterial cell a cDNA sequence that encodes a gene product that results in a particular phenotype upon contact with a test substance. The restriction site may be selected from a number of known restriction sites.

The cDNA sequences isolated from the bacterial cells in the final step of the method described above can then be processed through the same steps additional times, by re-introducing the isolated cDNA sequences into a new population of nucleic acids as set forth in the present invention, wherein the nucleic acid comprises a retroviral LTR comprising a loxP site or a restriction site in the U3 region; introducing said nucleic acids into eukaryotic cells; contacting the cells with a test substance; introducing a nucleic acid encoding Cre protein into cells having the particular phenotype, under conditions whereby the Cre protein nucleic acid is expressed; extracting circular DNA from the eukaryotic cells; transforming a bacterial cell with the circular DNA; and isolating from the bacterial cell a cDNA sequence that encodes a gene product that results in a particular phenotype upon contact with a test substance. The steps are repeated on a new population of cDNA sequences that are selected for the ability to impart a particular phenotype on a cell upon exposure to a test substance, in order to generate or identify cDNA sequences that are mutated and are therefore even more capable than previous cDNA sequences to produce a particular phenotype in a cell under the selective pressure of the test substance. These cDNA sequences can then be further characterized and the gene product identified which has the observed effect on the phenotype of the cell.

In another embodiment, the cDNA library employed in the methods described above can be produced by cloning the KM fragment of this invention into standard non-retroviral expression cassettes comprising a cDNA library.

This method can also be employed on known coding sequences instead of a cDNA library, to identify mutants that produce a particular phenotype in a cell under the selective pressure of a, test substance. For example, the known coding sequence can be a gene for antibiotic resistance and the test substance can be varying concentrations of the specific antibiotic to which the gene product imparts resistance. By employing several rounds of the steps of the described method with increasing concentrations of antibiotic, a mutated gene that imparts resistance to high concentrations of the antibiotic can be identified and isolated.

The polypeptide sequences isolated from the bacterial cells in the final step of the method described above can then be processed through the same steps additional times, by re-introducing the isolated polypeptide sequences into a new population of vectors as set forth in the present invention, wherein the vector comprises a retroviral LTR comprising a loxP site or a restriction site in the U3 region; introducing said vector into eukaryotic cells; contacting the cells with a test substance; introducing a vector encoding Cre protein into cells having the particular phenotype, under conditions whereby the Cre protein vector is expressed; extracting circular vectors from the eukaryotic cells; transforming a bacterial cell with the circular vectors; and isolating from the bacterial cell a polypeptide sequence that encodes a gene product that results in a particular phenotype upon contact with a test substance. The steps are repeated on a new population of polypeptide sequences that are selected for the ability to impart a particular phenotype on a cell upon exposure to a test substance, in order to generate or identify polypeptide sequences that are mutated and are therefore even more capable than previous polypeptide sequences to produce a particular phenotype in a cell under the selective pressure of the test substance. These polypeptide sequences can then be further characterized and the gene product identified which has the observed effect on the phenotype of the cell.

The particular phenotype to be observed or detected in the above-described method can be, but is not limited to, cell death, change in cell morphology and/or cell size, change in cell mobility, change in chemotactic activity, and/or change in a specific metabolic process within the cell that is detectable (e.g., cell division, nucleic acid synthesis, mRNA profile, etc.).

Furthermore, the methods of this invention whereby a cDNA sequence can be identified and isolated can be performed using DNA extraction protocols that do not employ the loxP/Cre system. For example, the cDNA library can be produced in nucleic acids of this invention that do not contain a loxP site or a restriction site in the U3 region of the LTR, but do contain specific primer sequences. These nucleic acids are introduced into eukaryotic cells; the cells are contacted with a test substance; the DNA is extracted from cells that produce a particular phenotype upon exposure to the test substance and amplified by PCR or other amplification techniques known in the art, using primers that hybridize to the specific primer sequences of the nucleic acids of the cDNA library; bacterial cells are transformed with the amplified DNA; and the cDNA sequences are isolated from the bacterial cells. In an alternative embodiment, the nucleic acids of this invention can contain a protein recognition site. These nucleic acids are introduced into eukaryotic cells; the cells are contacted with a test substance; the DNA is extracted from cells that produce a particular phenotype upon exposure to the test substance; the DNA is run through a column containing a protein which binds the protein recognition site on the nucleic acids; bacterial cells are transformed with the DNA bound to the protein; and the cDNA sequences are isolated from the bacterial cells.

Another example of the present invention can include a method of isolating a nucleic acid that encodes a gene product. The single-LTR vector can be used to identify functions of domains or sequences within a gene or a protein. A cDNA library can be constructed from mRNA obtained from appropriate genes, proteins, cells or tissues derived from an organism of interest. A labeled fragment may be used to screen a genomic library derived from the organism of interest using appropriately stringent conditions well known to those of skill in the art. The single-LTR vector can allow for the identification of domains within a protein to determine activity of a protein as well as the ability to identify targets of new drugs. A single-LTR vector can also be used to identify both dominant positive and negative mutants as well as gene expression and gene regulation. The single-LTR vector can also be used to identify promoters, gene expression, splicing, etc. in a gene or protein.

For example, the amplified fragment may be labeled and used to screen a cDNA library, such as a bacteriophage cDNA library. Alternatively, the labeled fragment may be used to isolate genomic clones via the screening of a genomic library. PCR technology may be utilized to isolate full length cDNA sequences. For example, RNA may be isolated, following standard procedures, from an appropriate gene or protein. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of PCR technology and cloning strategies which may be used, see e.g., PCR Primer, 1995, Dieffenbach et al., ed., Cold Spring Harbor Laboratory Press; Sambrook et al., 1989.

Another example of the present invention can include a method of isolating a nucleic acid that encodes a gene product. A genomic library may be utilized to study the effects of the single-LTR vector. A genomic library can include a collection of cloned DNA fragments which, taken together, represent the entire genome of a specific organism. Such libraries or "gene banks" can be assembled to allow the isolation and study of individual genes. Genomic libraries are produced by first breaking up or "fractionating" an entire genome. This fractionation can be accomplished either by physical methods or by use of restriction enzymes. The genome fragments are then cloned (multiplied in number) and stored for later use. Libraries of different genes and their associated mutations may be used. The genes studied may include important domains within the gene as well as dominant positive and dominant negative mutants. The single-LTR vector can allow for the identification of domains within a protein to determine activity of a protein as well as the ability to identify targets of new drugs. A single-LTR vector can be used to identify both dominant positive and negative mutants. The single-LTR vector can be used to identify promoters, gene expression, splicing, etc. These mutants can be characterized to determine if the protein suppresses or increases gene function, i.e. affects transcription, translation, mRNA synthesis, etc.

Another aspect of the present invention includes a self-inactivating (SIN) version of the single-LTR vector. This vector can be generated by a transient three-plasmid transfection in titers comparable to the parental non-SIN vector. This is possible through the initiation transcription of full-length vector RNA from an aberrant transcription initiation site in non-integrated vector DNA. The unique structure of the single-LTR vectors can allow for the identification of a continuous DNA sequence (KM fragment), which contains all the cis elements required for efficient vector production. Incorporating the KM fragment into expression cassettes results in the generation of new HIV-1 vectors by a single cloning step, which imparts a simplified procedure of converting simple cDNA expression cassettes into single-LTR lentiviral vectors. Further optimization of the single-LTR vector for functional genomic applications can include the incorporation of a LoxP site and a restriction-enzyme site, such as SbfI, into the vector LTR. These modifications can allow for the rescue of integrated vector genomes into individual bacterial clones. Vector DNA was isolated from bacteria by a simple plasmid purification procedure and was used to generate high titer vector particles ready for a second round of functional screening.

Having described the present invention, the same will be explained in greater detail in the following examples, which are included herein for illustration purposes only, and which are not intended to be limiting to the invention.

EXAMPLES

Example I

Figure 6:
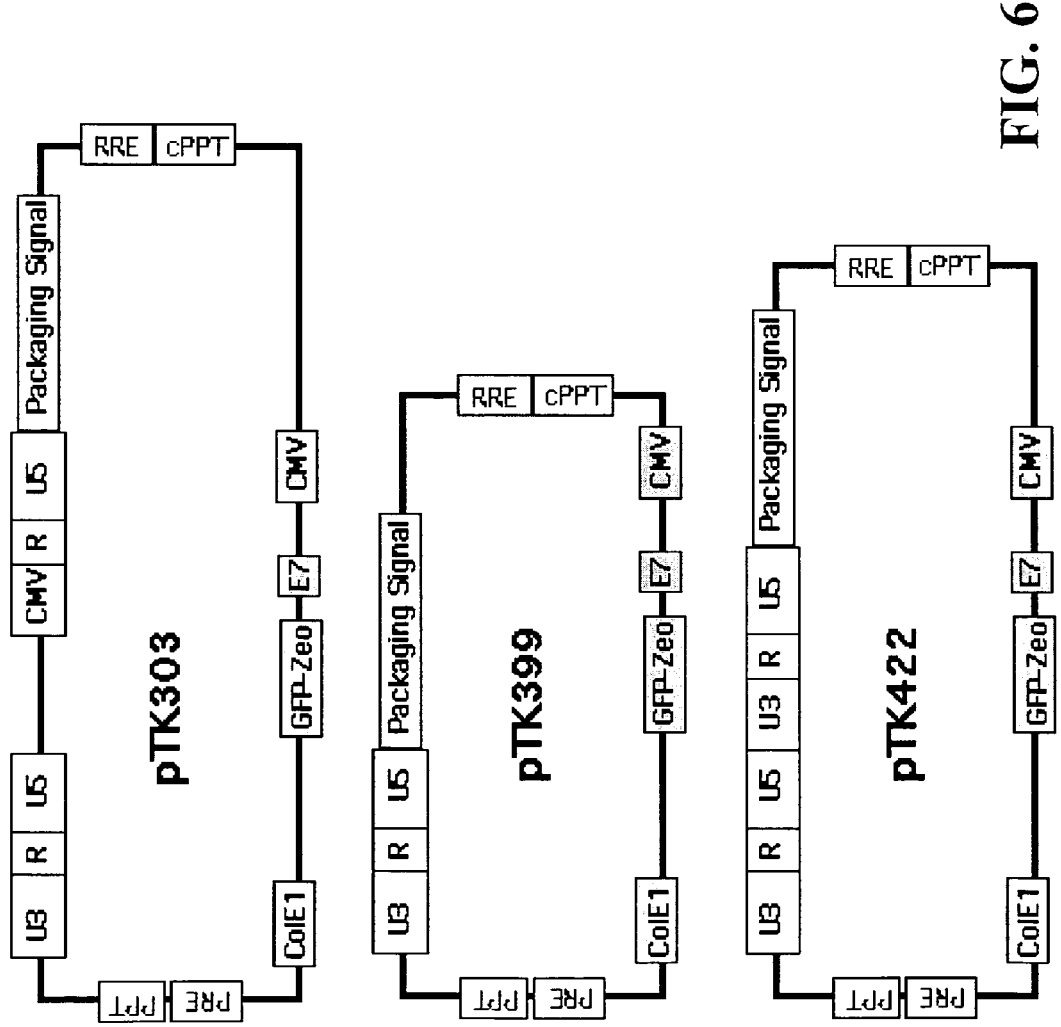
FIG. 6 illustrates examples of normal, single and double LTRs produced by transfection, and that episomal vectors allow for the production of integrating vector particles for both one and two LTRs.
Figure 7:
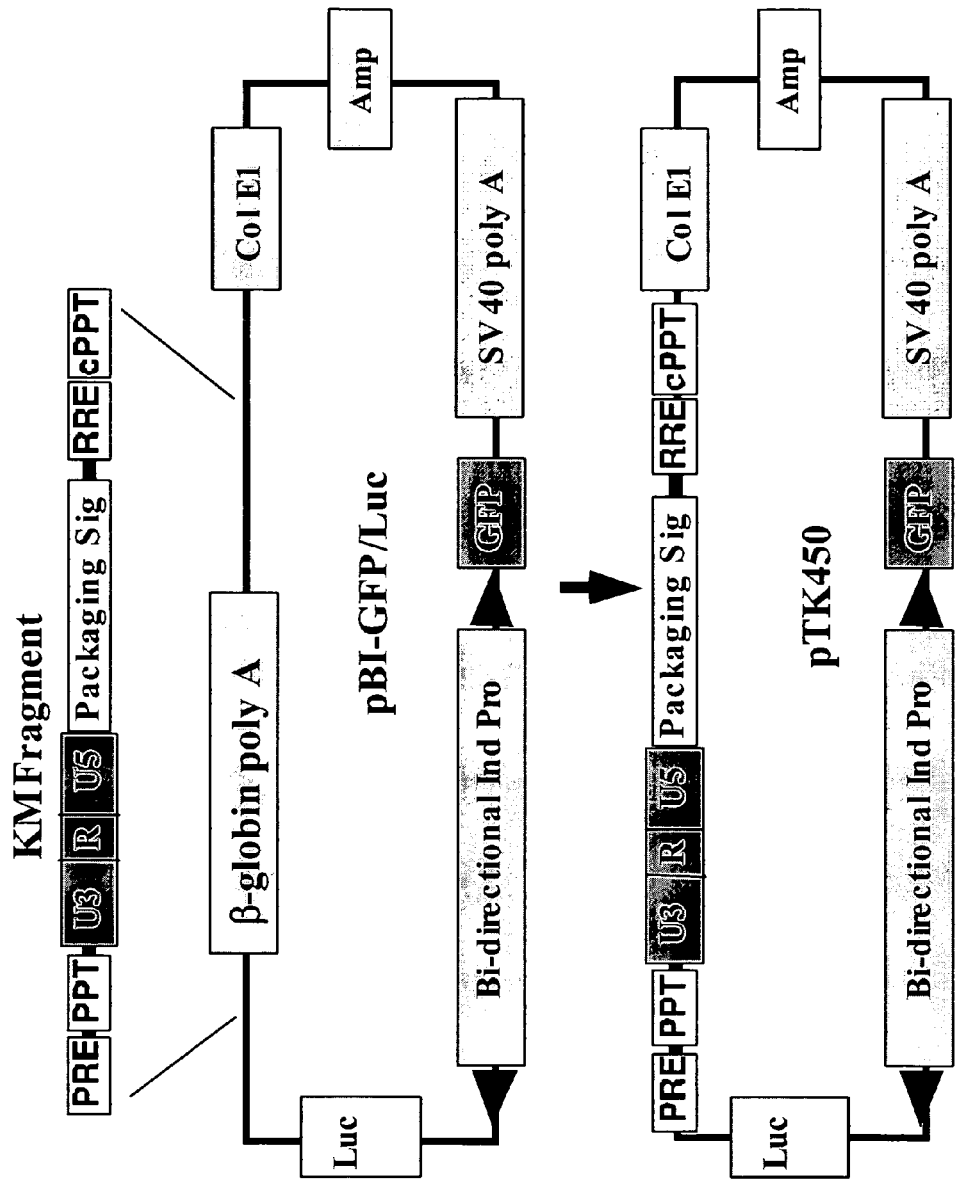
FIG. 7 depicts conversion of an expression cassette into a retrovirus vector by replacing the polyadenylation signal with the KM fragment.

To facilitate the characterization of the mechanism involved in the formation of non-integrated circular HIV-1 DNA forms, the present invention provides an HIV-1 shuttle vector (pTK303) which allows for the clonal isolation of circular vector DNA in bacteria. As shown in FIG. 6, the vector contains the GFP/Zeocin fusion protein gene under the control of the CMV and the bacterial E7 promoters. The ColE1 bacterial origin of replication that supports a plasmid-like replication in bacteria was also incorporated between the LTRs of the vector. High titers of vector particles were generated by co-transfecting the pTK303 DNA construct with HIV-1 packaging and a VSV-G envelope expression cassettes into 293T cells. Although transduction efficiency of the shuttle vector particles was found comparable to that obtained from traditional HIV-1 vectors, the level of transgene expression as determined by FACS analysis, was lower than that observed from a traditional CMV promoter containing HIV-1 vector (pTK113).

Using the shuttle vector, the ratio by which the different circular HIV-1 forms are generated either in the presence or the absence of viral integrase activity was determined.

Figure 3:
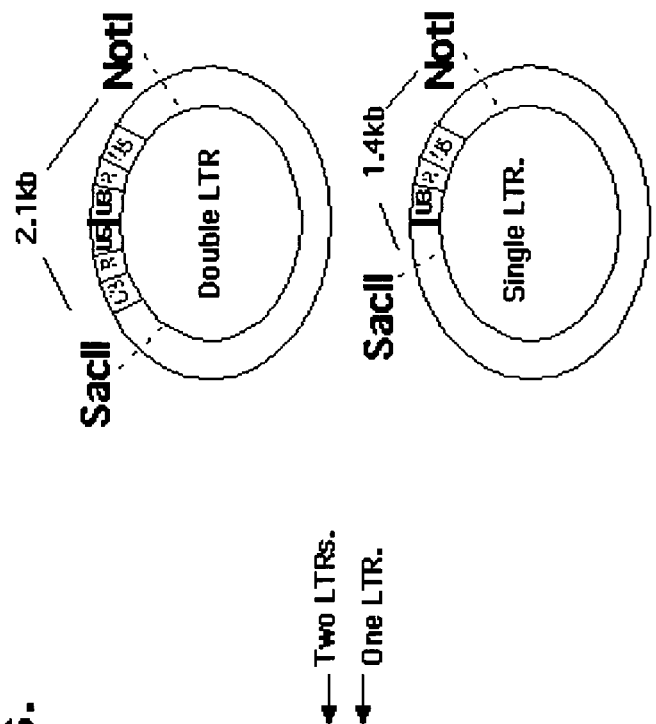
FIG. 3 demonstrates a restriction digest analysis of episomal lentivirus vectors containing one and two LTRs.
Figure 3:
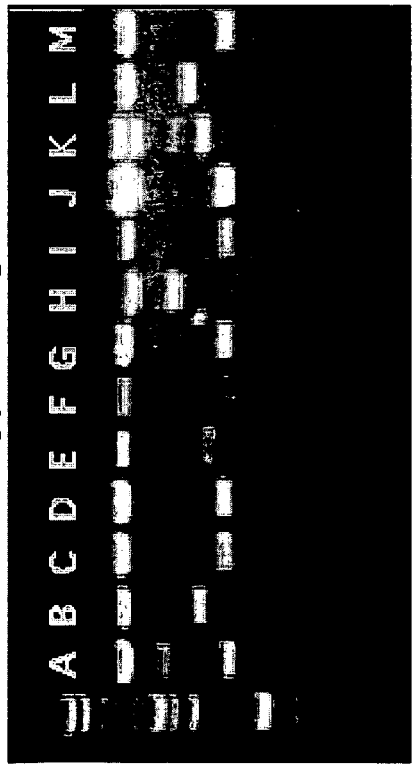
Figure 3:
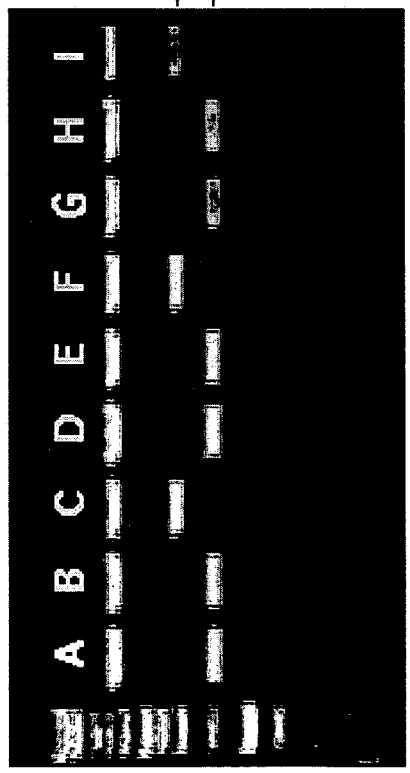

293T cells were transduced with VSV-G pseudotyped vector particles containing either the wild type HIV-1 integrase or its E152A mutant. Earlier studies which characterize this mutant in the context of the HIV-1 virus demonstrated a complete loss of integration activity while all other steps in the virus life cycle including reverse transcription and nuclear import were not affected. At 12 h post transduction, circular HIV-1 vector forms were isolated by DNA HIRT extraction and electroporated into bacteria. Following bacterial colony selection with Zeocin, 100 circular vector DNA clones were isolated by a simple plasmid extraction protocol. Using a DNA restriction analysis on each of the isolated DNA clones, the ratio by which 1,2-LTR and mutant circles were formed was determined. As shown in FIG. 3, most of the circular vectors forms (72%) were generated by homologous recombination and contained 1 LTR. 13% of the circular forms were generated by end to end ligation of the LTRs of the vectors and thus contained 2 LTRs. Up to 15% of the cloned circles were formed by an integrase-mediated autointegration reaction and demonstrated restriction digest patterns which were not compatible with full-length circular vector forms. These forms were termed "mutant circles." Because the formation of the mutant circles is integrase dependent, it was not surprising that their ratio in the circular HIV-1 forms decreased dramatically (from 15 to 3%) when the vector particles contained the mutant integrase. It was also observed that the fraction of the 1-LTR vector forms did not increase in integrase mutant transduced cells, but the percentage of the 2-LTR circular vector forms increased from 13% to 30%. Further characterization of the 1-LTR and 2-LTR isolated vector forms by sequence analysis demonstrated the predicted 1 and 2 LTR structures without any mutation in the LTRs or in the vector junction sequences of the LTRs.

To determine whether full-length vector RNA can be efficiently transcribed from circular vector forms and packaged into productive vector particles, the isolated 1-LTR (pTK399) and 2-LTR (pTK422) circular vector forms were transfected, together with HIV-1 packaging and VSV-G envelope expression cassettes, into 293T cells. Vector particles were collected at 72 h post-transfection. Transgene expression and vector titer were determined by FACS analysis and serial dilution on 293T cells. As shown in FIG. 6, transgene expression and vector titer generated by the 1 and 2-LTR circular forms were comparable with or higher than those obtained from a traditional vector (pTK303) containing two separated LTRs.

Figure 4:
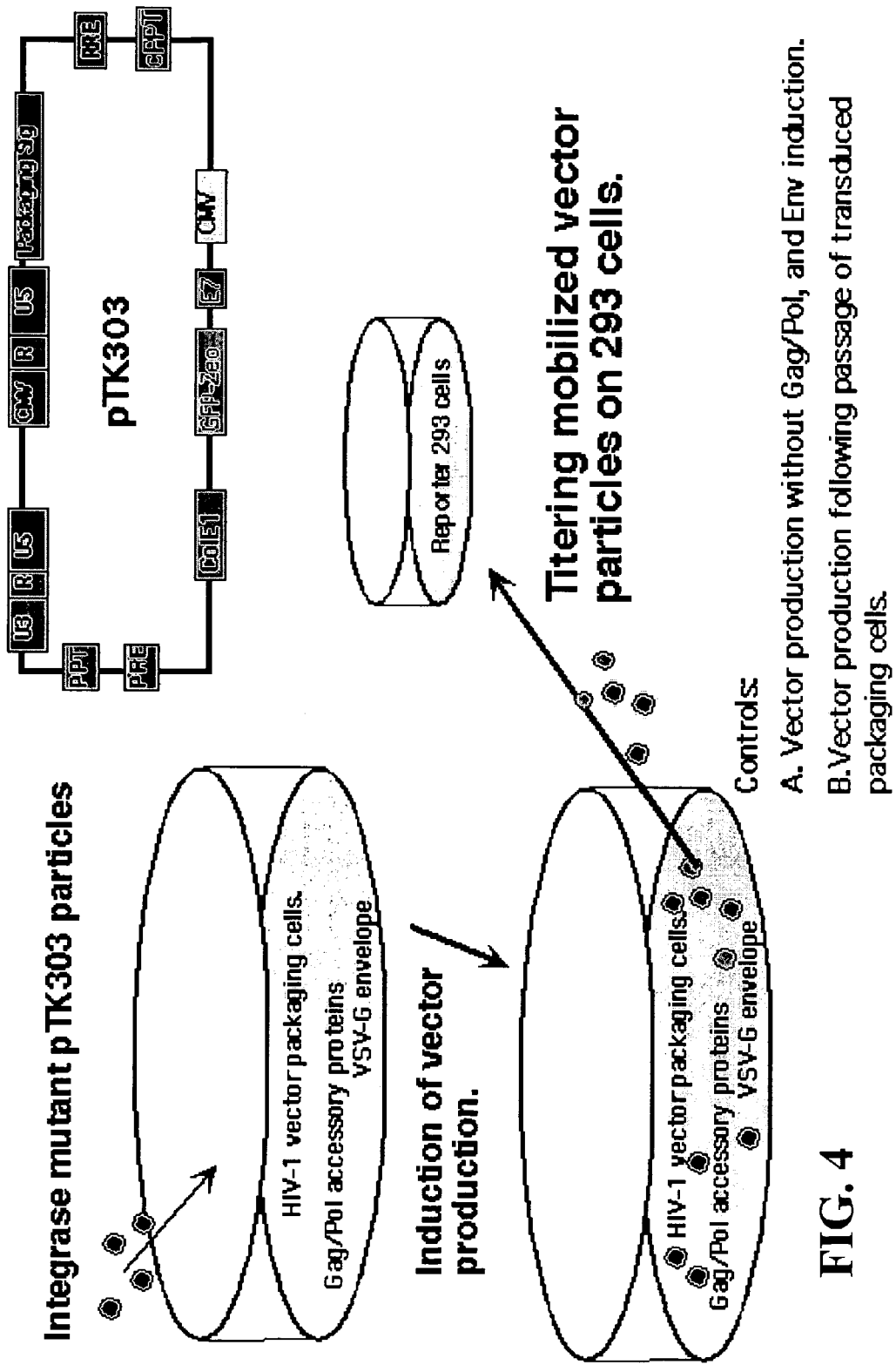
FIG. 4 depicts the mobilization of an episomal HIV-1 vector.

Being aware of the fact that transfection of circular vector DNA may not accurately reflect the ability of episomal vector DNA forms generated in the process of vector transduction to be rescued, the efficiency by which non-integrated vectors can be rescued from a packaging cell line following transduction was determined. To this aim, SODk1 packaging cells expressing the VSV-G envelope and all the HIV-1 genes (excluding the HIV-1 env gene), under the control of a tetracycline inducible promoter, were transduced with vector particles packaged with the E152A integrase mutant. (FIG. 4). At 48-hr post-transduction, packaging cell line-generated vector particles were collected and titered by scoring GFP expression following serial dilution on 293T cells. Vector titers were found to be in the range of $1-2 \times 10^4$ IU/ml. (FIG. 5) Transgene expression level was comparable to that obtained from similar vectors containing wild type integrase and was stable for more than 4 weeks (the duration of the experiment). These findings indicated that full-length vector RNA was efficiently transcribed from episomal vector forms and packaged by SODk1 cells into wild type integrase-containing vector particles. The fact that a minimal number of vector particles (titer<$10^2$ IU/ml) could be recovered from non-induced SODk1 cells ruled out the possibility that carry over of the E152A integrase mutant-containing vector particles was mistakenly analyzed as newly synthesized vector particles.

Figure 5:
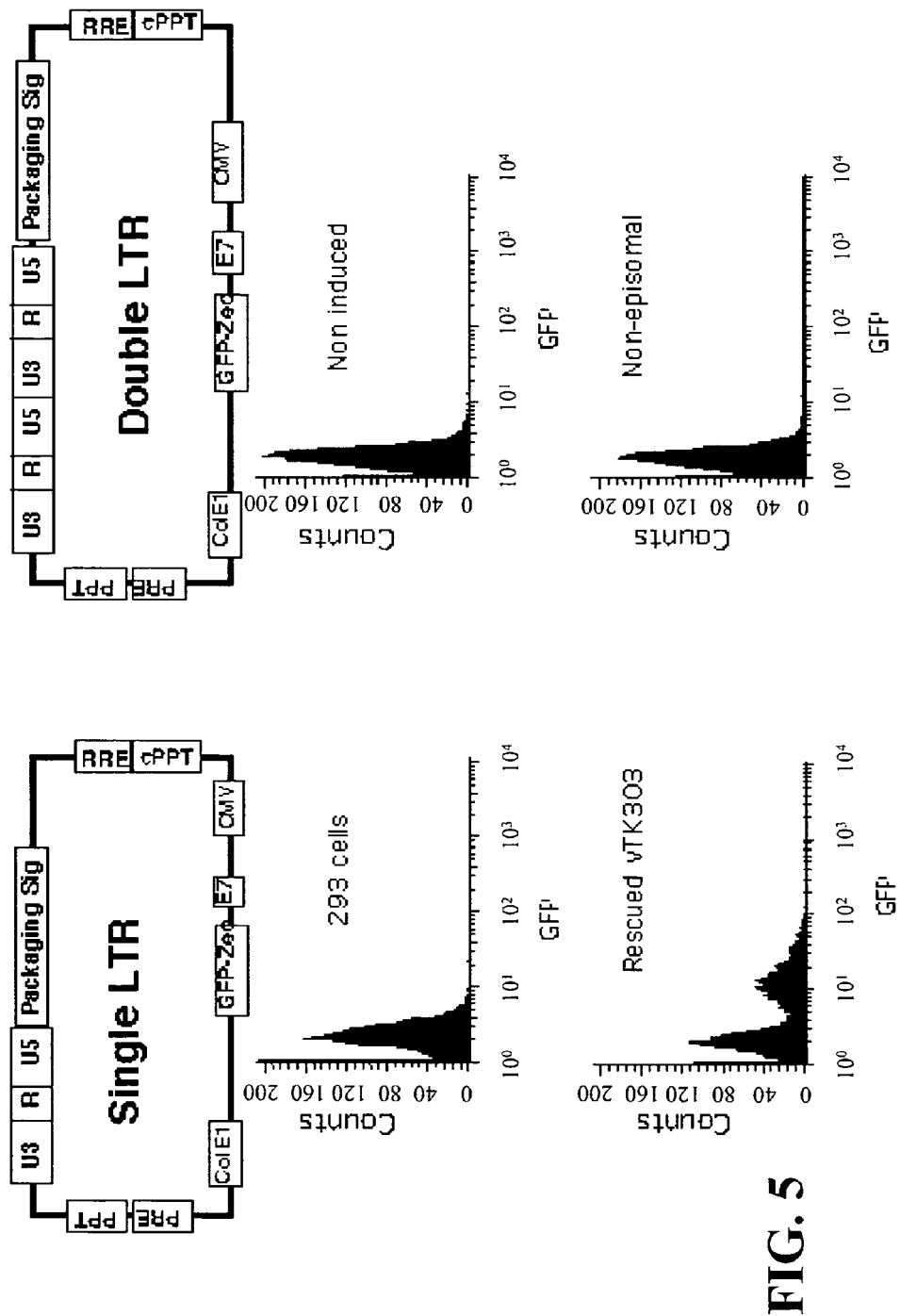
FIG. 5 demonstrates that the induction of transduced SODk1 cells following 4 weeks of culture resulted in minimal production of vector particles.

To rule out the possibility that vector particles were generated from integrated vectors following non-legitimate recombination, SODk1 cells transduced with the integrase mutant-containing particles were cultured for four weeks, during which the non-replicating, non-integrated circular vector DNA forms were diluted out. As shown in FIG. 5, induction of transduced SODk1 cells following 4 weeks of culture resulted in minimal production of vector particles (titer<$10^2$ IU/ml), which could not be detected by FACS analysis. This result indicated that the production of integrating vectors by SODk1 cells shortly after being transduced with integrase mutant-containing particles was based on non-integrated vector DNA structures which were transcribed to packagable full-length vector RNA.

The incorporation of a bacterial promoter and an origin of replication between the vector LTRs (pTK303), which was required for the isolation and amplification of a single LTR containing shuttle vector, resulted in a significant reduction in transgene expression. CMV-controlled expression of the GFP marker gene from the pTK 303, pTK 399 and pTK 422 vectors is significantly lower than GFP expression from the traditional vector pTK 113. To improve transgene expression from a single LTR containing vector, a new shuttle vector, pTK469, was developed in which the bacterial promoter was separated from the CMV promoter and the GFP reporter gene. GFP expression in pTK469-transduced cells was significantly higher than its expression in pTK303-transduced cells and almost comparable to the level of expression obtained from the traditional vector, pTK113.

Using the Hirt DNA extraction method, two and single-LTR circular HIV-1 vector forms were isolated from pTK459-transduced 293T cells. The isolated circular vector DNA clone pTK469 (containing a single-LTR) was used in a transient three-plasmid transfection to generate high titer infectious vector particles ($3-4 \times 10^6$ IU/ml). The level of GFP expression from pTK469-transduced cells was comparable to GFP expression in 293T cells transduced with the parental vector pTK459.

Figure 10:
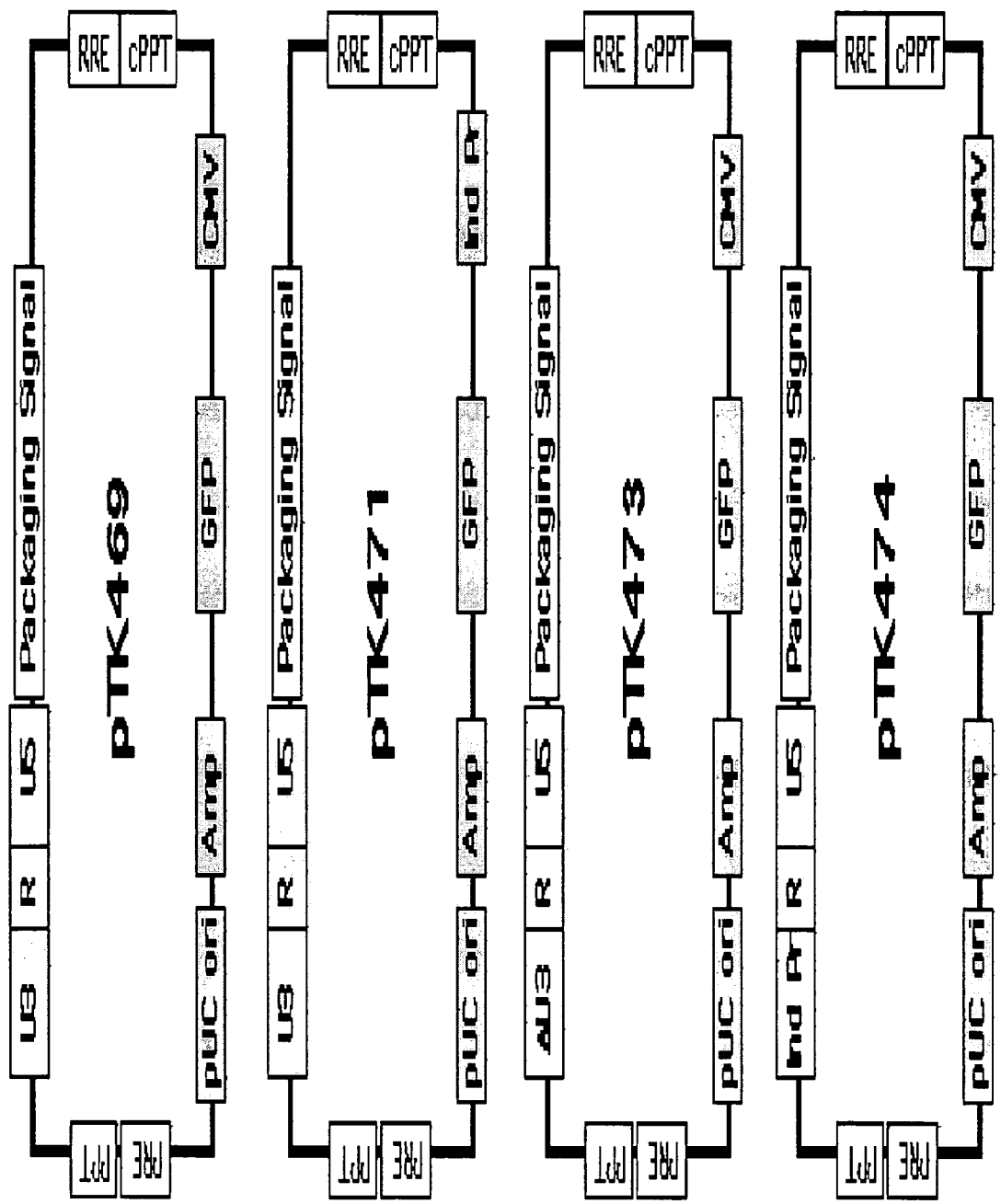
FIG. 10 depicts various single LTRs.
Figure 11:
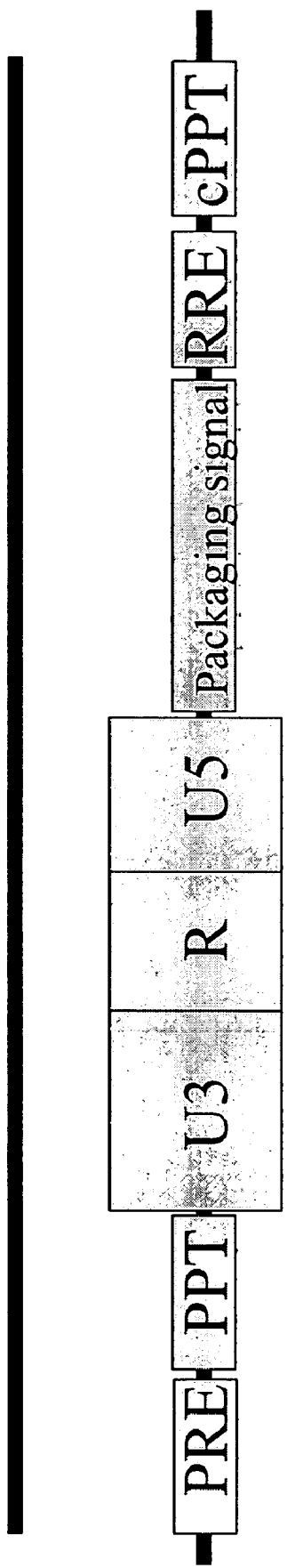
FIG. 11 illustrates the extended KM fragment comprising the PRE and the cPPT.
Figure 12:
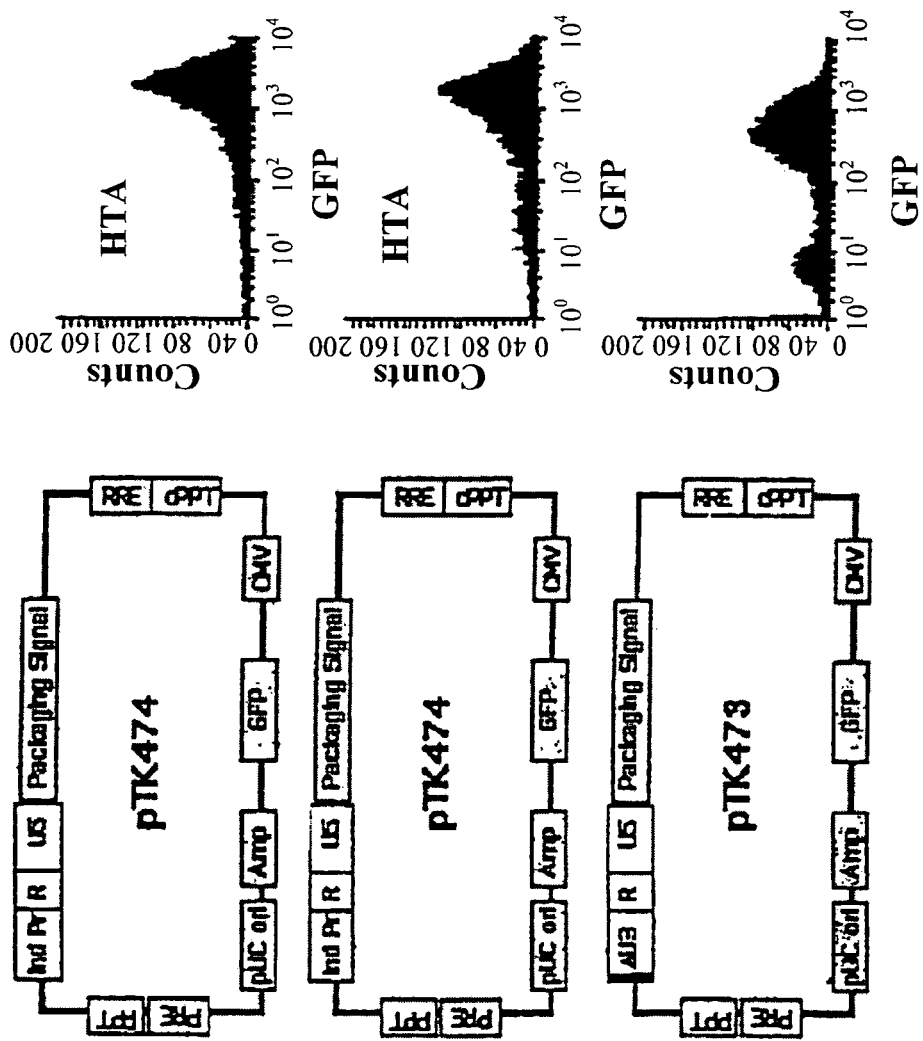
FIG. 12 depicts self-inactivating (SIN) single LTR lentivirus vectors.

A major improvement in the safety of the lentivirus vector gene delivery system was based on the development of self-inactivating (SIN) vectors in which the majority of the 3' U3 region, including the HIV-1 enhancer/promoter sequences was deleted. Since in the process of reverse transcription, the modified 3' U3 region is transferred to the 5'LTR, integrated SIN lentivirus vectors are devoid of the ability to transcribe full-length vector RNA. Thus a SIN vector is less likely to recombine into a replication competent virus or to be mobilized following an infection with a wild type virus. Incorporating the SIN feature into the single-LTR based vector system required the development of a conditional SIN vector pTK474 in which the parental U3 region containing the HIV-1 enhancer/promoter sequence was replaced with a tetracycline-inducible promoter. This design was based on the idea that in tetracycline-regulated transactivator (tTA) expressing cells, a conditional SIN LTR would support efficient transcription of packagable full-length vector RNA, while in target cells that do not express the tTA, vector production will be minimal even in the presence of all the HIV-1 gene products. To test this hypothesis, the conditional SIN single-LTR vector vTK474 (FIG. 10) was generated by transient transfection of the pTK474 plasmid into 293T cells, along with an HIV-1 packaging construct, a VSV-G envelope expression vector and a tTA expression cassette. A vector titer of $2-3 \times 10^6$ IU/ml was determined by scoring GFP expression following serial dilution on 293T cells. Attempts to rescue vector particles by transfecting vector-transduced 293T cells with a VSV-G envelop and an HIV-1 packaging construct yielded a titer of $8-12 \times 10^2$ IU/ml. A similar rescuing procedure of the non-SIN vector vTK369 yielded a titer of $2-3 \times 10^6$ IU/, indicating that the conditional-SIN single-LTR vector, which was generated in high titer in tTA-expressing cells, retained its SIN feature in target cells which did not express the tTA.

The development of tetracycline inducible system-containing lentivirus vectors broadened the spectrum of lentivirus vector applications in clinical and research setting, since it conferred the ability to regulate transgene expression in vivo. This desirable feature was incorporated into the single-LTR vector pTK 471 (FIG. 10), in which GFP expression was controlled by an internal tetracycline-regulated promoter. A vector titer of $2-3 \times 10^6$ IU/ml was determined by scoring GFP expression following serial dilution on tTA-expressing 293T cells. Expression of the GFP reporter gene may then be efficiently turned off by adding doxycycline to the culture medium, thus demonstrating the ability to efficiently regulate transgene expression in tTA-expressing cells.

Figure 8:
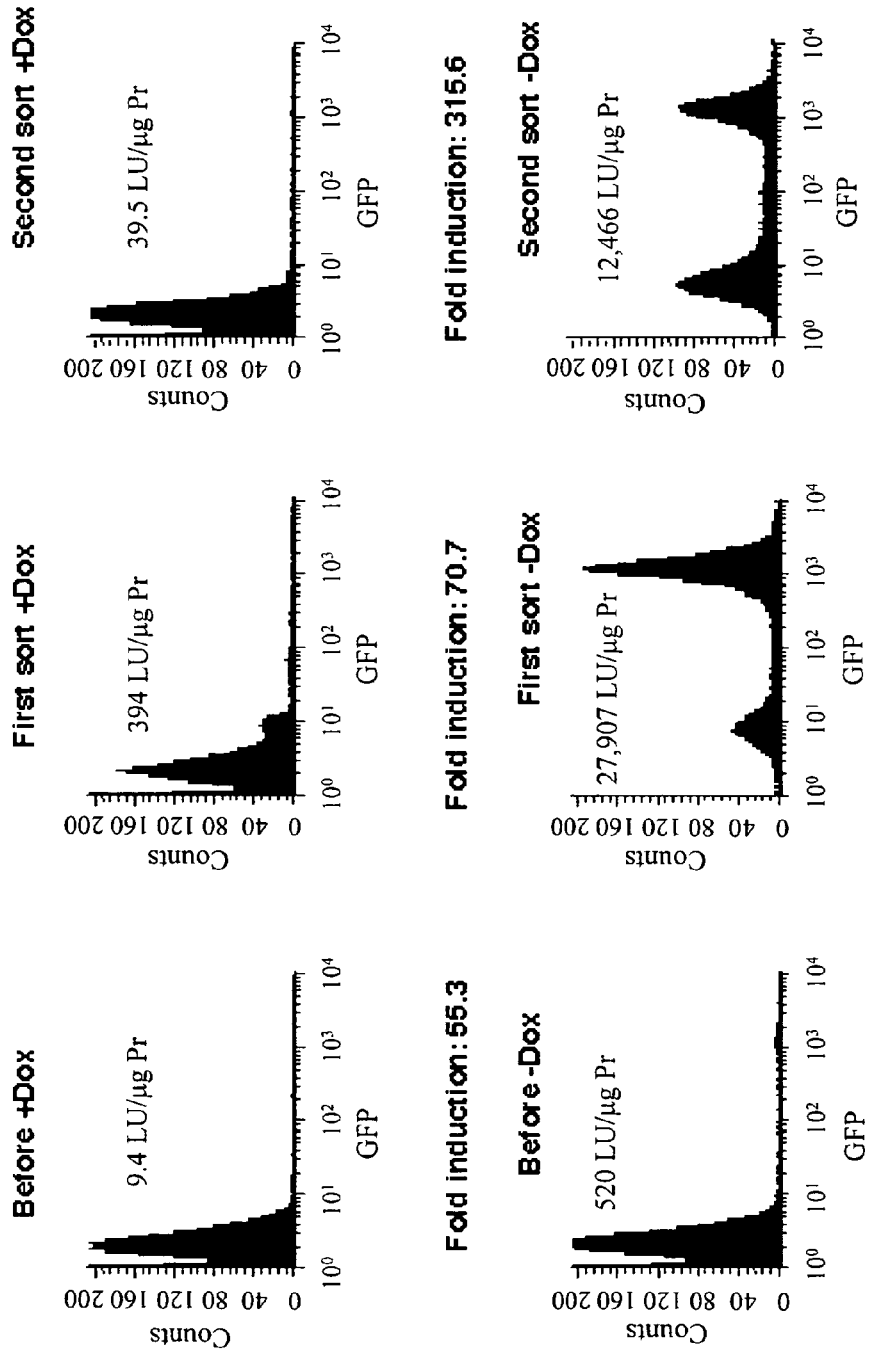
FIG. 8 shows FACS enrichment of tightly regulated transgene expression from a Bi-directional inducible lentivirus vector.
Figure 9:
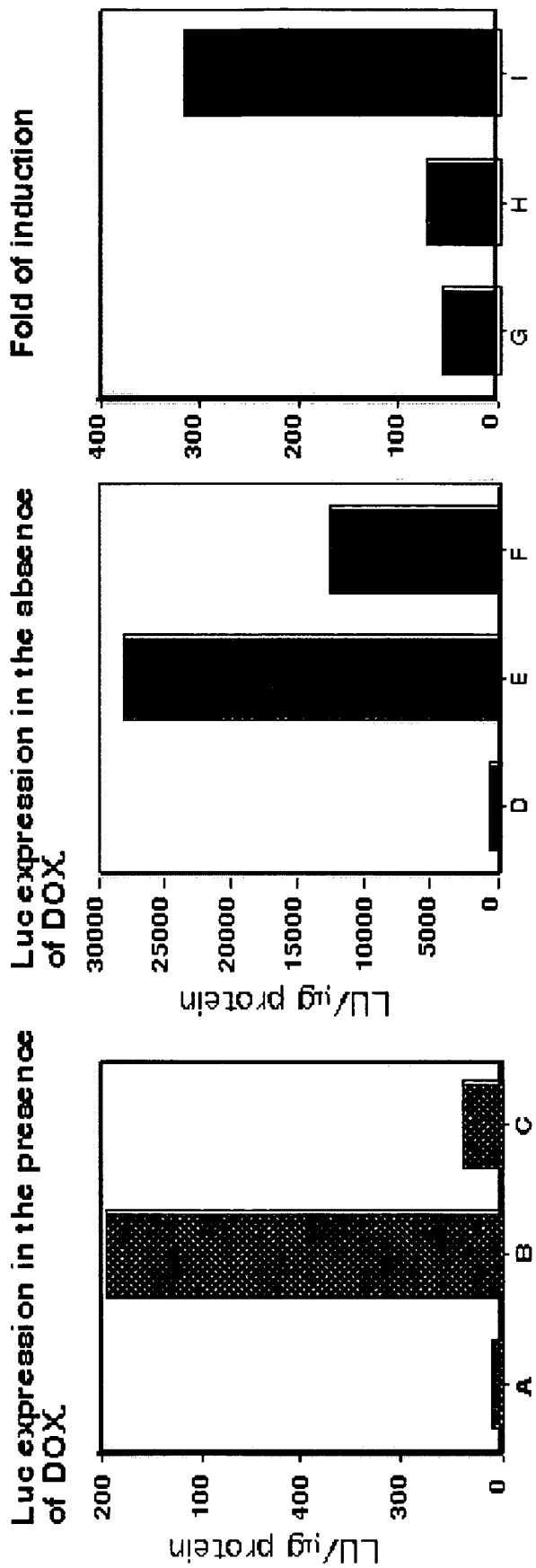
FIG. 9 demonstrates FACS enrichment of 293T cell that exhibit inducible Luc expression.

The fact that a single LTR-containing vector could be generated in high titer indicated that a single DNA fragment could contain all the cis acting sequence required for efficient production of infectious vector particles. To test this hypothesis, a 3kbp DNA fragment (KM fragment) was isolated, from the single-LTR vector pTK469. This fragment contained the following cis elements (from 5' to 3'): the woodchuck hepatitis virus post-transcriptional regulatory element (PRE), and HIV-1 sequences including the 3' polypurine tract (PPT), the HIV-1 LTR, the packaging signal, the Rev response element (RRE), and the central polypurine tract (cPPT). A new bi-directional inducible lentivirus vector, pTK441, was generated by cloning the KM fragment into the pBI-GFP expression cassette (Clontech) in which GFP expression is regulated by a bidirectional tetracycline inducible promoter. The cloning of the firefly luciferase gene under the control of the bi-directional promoter into pTK441 vector may be generated the single-LTR vector pTK450, in which a bi-directional tetracycline inducible promoter regulates the expression of both the firefly luciferase gene and the GFP marker gene. Vector particles were generated by transient three plasmid transfection in 293T cells. A vector titer of $2-3 \times 10^4$ IU/ml was determined by scoring GFP expression following serial dilution on tTA-expressing 293T cells. Using three rounds of FACS-based sorting for GFP expression in the absence of doxycycline and for GFP negative cells in presence of doxycycline, it was possible to enrich for high GFP/luciferase expressing cells in which transgene expression was tightly regulated by doxycycline. As shown in FIGS. 8 and 9, luciferase induction rate, as determined by the ratio of luciferase expression in the absence and presence of doxycycline, increased with each round of sorting, starting with 30 fold induction shortly after transduction to up to 300 fold of induction following the next three rounds of sorting. This indicated that combining a bi-directional inducible promoter with FACS sorting facilitated the ability to tightly regulate transgene expression in heterogeneous cell population in vitro.

Example II

The incorporation of a bacterial origin of replication and an antibiotic resistance marker gene into a single-LTR retroviral vector cassette facilitated the isolation of integrated vector DNA in bacterial clones. This feature allows for the single-LTR vector system as it allows for efficient recovery of functional cDNAs. To optimize the single-LTR HIV-1 vector system for functional genomic applications, a LoxP site and an Sbf1 restriction site were incorporated into the U3 region of a SIN single-LTR HIV-1 vector. Expression of the GFP-blastocidin fusion gene from this novel vector (pTK589) was under the control of a CMV promoter. Vector particles were generated at a titer of $1-2 \times 10^6$ IU/ml, and conferred blastocidin resistance to transduced 293T cells. To recover and isolate vector DNA, $2 \times 10^6$ blastocidin-resistant cells were transfected with the Cre expression plasmid pTK601. At 12 hr post transfection episomal circular vector DNA was purified by Hirt extraction and used to transform bacteria of which 150 isolated clones showed ampicillin resistance. Using a small-scale plasmid extraction method eight rescued vector clones were purified and all showed restriction digest patterns identical to the ones obtained from the parental vector pTK589. Vector particles were generated with the rescued vector DNAs at titers comparable ($1-2 \times 10^6$ IU/ml) to the titers obtained with the parental vector DNA and allowed efficient GFP-blastocidin gene expression in 293T target cells. To circumvent the need of expressing the Cre gene in vector transduced cells, two alternative approaches were tested by which integrated vector DNA could be rescued in-vitro from host cell genome. Genomic DNA (1 µg) extracted from vector-transduced cell was either treated in-vitro with the Cre-recombinase protein (Clontech), or subjected to SbfI restriction enzyme digestion, which followed by self-ligation. The Cre and SbfI treated DNAs were used to transform bacteria from which 75 and 85 ampicillin resistant clones were isolated respectively. Using small-scale plasmid purification method we isolated 10 vector DNA clones, which were subjected to restriction digest analysis. Six and eight out ten DNA clones generated by the in-vitro Cre and SbfI digest method, respectively, exhibited restriction-digest pattern identical to that of the parental vector pTK586 and could support production of comparable vector titers.

Example III

Self Inactivating Vectors

The incorporation of the Self Inactivating Vector (SIN) feature into the single-LTR based vector system includes the development of a conditional-SIN vector, such as pTK474, in which the parental U3 region containing the HIV-1 enhancer/promoter sequence was replaced with a tetracycline-inducible promoter. The conditional SIN single-LTR vector vTK474 was generated by transient transfection in the presence of a tTA expression cassette. A vector titer of $2-3 \times 10^6$ IU/ml was determined by scoring GFP expression following serial dilution on 293T cells. Attempts to rescue vector particles by transfecting vector-transduced 293T cells with a VSV-G envelope and an HIV-1 packaging construct yielded a titer of $8-12 \times 10^2$ IU/ml. In comparison, a similar rescuing procedure using 293T cells transduced with the non-SIN vector vTK469 yielded titer of $2-3 \times 10^6$ IU/ml, thus indicating that the conditional-SIN single-LTR vector retained its SIN feature following integration in target cells. However, the titer of the conditional SIN vector vTK474 generated by transient transfection was not affected by the absence of the tTA expression cassette. Thus, the possibility that the U3 enhancer promoter sequences of a single LTR vector are dispensable for efficient vector production by transient transfection was explored. Tthe SIN single-LTR vector pTK485 was constructed from which the enhancer promoter sequences containing the TATA box, NF-kB and Sp1 recognition sites were deleted. Production of the SIN vector by transient transfection yielded titer of $2-3 \times 10^6$ IU/ml, which was comparable to titers of non-SIN vectors, and confirmed that the U3 enhancer/promoter sequences including the parental HIV-1 TATA box are not essential for efficient vector production by transient transfection. To determine whether the vector RNA was transcribed from integrated vector genomes or from episomal vector DNA structures the transduced packaging were cultured for four weeks during which the episomal vector forms have been diluted out. Induction of vector production by the of the cultured packaging cells yielded vector particles at titer of only $1-2 \times 10e2$ IU/ml, which indicated that the majority of the SIN vector-RNA was transcribed from non-integrated vector DNA.

A 5'-RACE analysis (Ambion) was then used to identify the transcription initiation site of packaged RNA molecules generated from non-SIN and SIN single-LTR vectors (pTK469 and pTK485 respectively). A pool of PCR amplified cDNAs generated by the 5'-RACE procedure was cloned into a TA-plasmid. This allowed for the identification of discrete vector RNA initiation sites by sequence analysis. As expected in 8 out of 9 RACE clones generated from the non-SIN vector vTK469 RNA, the vector RNA initiation site was located toward the beginning of the R region. In one clone however, an alternative transcription initiation site was identified 181 bases upstream to the beginning of the R region. 9 out of the 9 RACE clones generated from the SIN vector vTK485 RNA, exhibited the same aberrant transcription initiation site, which due to the deletion in the U3 region was located 56 bases upstream to the beginning of R. These results indicate that the definition of the R region of HIV-1 vectors generated from circular episomal forms is flexible. The fact that an aberrant transcription initiation site was identified in one of the vTK469 RACE clones illustrates that this phenomenon is not restricted to SIN vectors and can have a role in natural life cycle of HIV-1.

In the specification, there has been disclosed typical preferred embodiments of the invention and, although specific terms are employed, they are used in a generic and descriptive sense only and not for purposes of limitation of the scope of the invention being set forth in the following claims.

What is claimed is:

1. An isolated nucleic acid comprising a heterologous nucleotide sequence, a single retroviral long terminal repeat (LTR), a packaging signal, a rev responsive element, a polypurine tract, a eukaryotic promoter, a primer binding site, a bacterial origin of replication and a bacterial selection marker, and wherein the U3 region of the LTR comprises a loxP site.

2. The nucleic acid of claim 1, fbrther comprising a central polypurine tract.

3. The nucleic acid of claim 1, further comprising a post-transcriptional regulatory element.

4. A vector comprising the nucleic acid of claim 1.

5. The nucleic acid of claim 1, wherein the U3 region of the LTR comprises a restriction site.

6. An isolated nucleic acid comprising a 5' retroviral LTR and a 3' retroviral LTR, a heterologous nucleotide sequence, a packaging signal, a rev responsive element, a polypurine tract, a eukaryotic promoter, a primer binding site, a bacterial origin of replication and a bacterial selection muter, wherein the bacterial origin of replication and bacterial selection marker are located between the two LTRs, and wherein the U3 region of the 3' LTR comprises a loxP site.

7. The nucleic acid of claim 6, fbrther comprising a central polypuxine tract.

8. The nucleic acid of claim 6, further comprising a post-transcriptional regulatory element.

9. The nucleic acid of claim 6, wherein the U3 region of the LTR. comprises a restriction site.

10. A method of making a retroviral vector particle, comprising:

a) introducing the vector of claim 4 into a retroviral packaging cell in medium, said packaging cell comprising nucleotide sequences encoding rev, gag/pol and env proteins but lacking packaging Sequences; and b) collecting retroviral vector particles from the medium.

11. A method of producing a retroviral expression vector, comprising cloning the nucleic acid of claim 1 into a non-retroviral expression vector.

12. The retroviral expression vector produced by the method of claim 11.

* * * * *